United States Patent

Christenson et al.

Patent Number: 5,144,048
Date of Patent: Sep. 1, 1992

[54] DICARBOALKOXY DIOXOLANE DERIVATIVES

[75] Inventors: Philip A. Christenson, Midland Park; Paul J. Riker, Lodi, both of N.J.; Denise A. Anderson, Brooklyn, N.Y.; John M. Yurecko, Jr., Dayton, N.J.

[73] Assignee: L. Givaudan & Cie, S.A., Geneva, Switzerland

[21] Appl. No.: 626,348

[22] Filed: Dec. 12, 1990

[51] Int. Cl.$^5$ .......................................... C07D 317/26
[52] U.S. Cl. ................................... 549/435; 549/448; 549/450; 549/454
[58] Field of Search .............. 549/435, 448, 450, 454

[56] References Cited

PUBLICATIONS

Chemical Abstract CA 108: 149914g, 1988.

Primary Examiner—C. Warren Ivy
Assistant Examiner—Ba K. Trinh
Attorney, Agent, or Firm—Richard R. Muccino; Robert F. Tavares; Linda Vag

[57] ABSTRACT

The present invention provides compounds which upon thermolyis, hydrolysis or both, release an odorant molecule. They find utility, for example, in tobacco, in tobacco paper, and as additives to food, beverages or gum. These compounds are dicarboalkoxy dioxolane derivatives having the following formula:

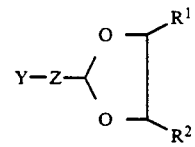

wherein $R^1$ and $R^2$ are, independently, $-CO_2R^3$ wherein $R^3$ is $-H_3$ or lower alkyl, provided that in at least one of $R^1$ and $R^2$, $R_4$ is lower alkyl; wherein Z is a direct bond, or $-CH=C(R^4)-$; where $R^4$ is an alkyl group; and Y is, when Z is a direct bond,

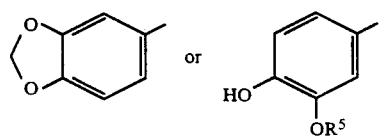

where $R^5$ is lower alkyl; and Y, when Z is $-CH=C(R^4)-$,

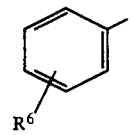

where $R^6$ is H, lower alkyl or $OR^7$, where $R^7$ is H or lower alkyl.

10 Claims, No Drawings

DICARBOALKOXY DIOXOLANE DERIVATIVES

FIELD OF THE INVENTION

The present invention relates to dicarboalkoxy dioxolane derivatives useful as flavor or fragrance precursor systems. More particularly, it relates to certain of these derivatives which are normally odorless but which upon thermolysis, hydrolysis or both, release an odorant molecule.

CROSS REFERENCE TO RELATED APPLICATIONS

Attention is directed to copending, commonly assigned U.S. application Ser. No. 395,628, filed Aug. 18, 1989, and entitled "NOVEL CYCLIC ACETALS" as well as to U.S. application Ser. No. [Attorney Docket No. 1315], filed [herewith], and entitled "ORGANOLEPTIC COMPOSITIONS."

BACKGROUND OF THE INVENTION

Flavor additives have long been used to flavor a wide variety of consumer products, particularly tobacco products, foodstuffs, and gums. Flavor additives in such products may be used to mask or attenuate undesirable flavors or odorants, and to enhance existing flavors or odors, or to provide additional flavors or odors not initially present in the consumer product.

A principal strategy currently employed to impart flavors or odors to consumer products is the admixing of the flavorant chemicals within a matrix that slows or prevents their release until the product is pyrolyzed, heated, masticated or wetted. Alternatively, the flavoring chemical may be covalently bound to an auxilliary component to form a higher molecular weight molecule of low volatility. The flavorant is then released upon pyrolysis, heating or solvolysis of the tobacco or food product. For example, European patent 186, 502 describes the use of a plastic capsule that releases flavorants when mechanically crushed.

U.S. Pat. No. 4,001,438 describes flavor compositions for use in orally utilizable compositions which may be either chewing gum compositions, chewable medicinal tablets, chewing tobacco or toothpaste. The flavor is controllably released from the flavor compositions over an extended period of time under hydrolytic conditions.

U.S. Pat. No. 4,253,473 describes smoking tobacco compositions or substitute smoking tobacco compositions which upon smoking release substantially evenly and uniformly over an extended period of time.

U.S. Pat. No. 3,818,107 describes a chewing gum containing a flavor release composition comprising polymer backbones with flavor groups appended thereto. The flavor moieties are released from the polymer backbone by hydrolysis which is achievable by mastication of chewing gums containing the flavor groups.

As an alternative method, the flavoring chemicals may be covalently bound to an auxilliary component to form a higher molecular weight molecule of low volatility. The flavorant is released upon pyrolysis, heating or solvolysis of the tobacco or food product.

In general, inventions employing the second strategy use an ester or carbonate linkage of a higher molecular weight molecule to an alcoholic flavor molecule. In such a system, a flavor molecule is covalently bound to a polymer and may be depicted by the following generalized structure:

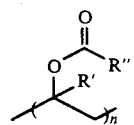

wherein R' represents a lower alkyl group such as methyl, R" represents a flavorant radical such as menthyl and n is an integer of from 2 to 10,000. This approach has been demonstrated in a number of U.S. Patents. For example, U.S. Pat. No. 4,212,310 describes different flavored smoking tobacco products wherein some of the products contain an alcohol flavorant-release composition which delivers the flavor note of the alcohol upon pyrolysis.

U.S. Pat. No. 4,119,106 describes alcohol flavorant-release polymeric derivatives which are designed to enhance tobacco smoke by releasing an alcohol flavorant to tobacco smoke without wasting the natural flavor of the resultant main stream tobacco smoke.

U.S. Pat. Nos. 4,578,486 and 4,538,628 describe smoking tobacco compositions which contain dioxane diester flavorant-release additives. When subjected to normal smoking conditions such as cigarettes, the diester additive decomposes to release a volatile pyrolysis (alcohol or phenol) component which provides flavor-enhancing properties to the mainstream smoke and enhances the aroma of the sidestream smoke.

U.S. Pat. Nos. 4,701,282, 4,538,627, and 4,540,004 describe the use of ketoester or carbonate compounds as flavorant additives which under cigarette smoking conditions pyrolyze to release flavorants which enhance the flavor of the mainstream smoke and the aroma of sidestream smoke.

Acetals have also been used as vehicles to covalently bind aldehyde flavorants. For example, U.S. Pat. No. 4,296,137 describes the use of 1-ethoxy-1-ethanol acetate as a flavor or fragrance enhancer of a wide variety of consumable materials. The 1-ethoxy-1-ethanol acetate compound has the ability to liberate acetaldehyde in smoking tobacco.

U.S. Pat. No. 4,280,011 describes the use of acetals as aldehyde generators in foodstuff applications.

U.S. Pat. No. 3,625,709 describes food flavoring and aroma enhancers consisting of acetaldehyde combined with carbohydrates to form compositions which release acetaldehyde when combined with hot water or with cold water.

U.S. Pat. No. 3,857,964 describes controlled release flavor compositions useful in flavor compositions which comprise flavor particles formed from a dispersion of flavor acetal or ketal in polymeric binders. The controlled release flavor compositions have multiple means of control, one of which is the hydrolysis of the flavor acetal or ketal. These controlled release flavor compositions are useful in chewing gums.

U.S. Pat. Nos. 4,690,157 and 4,607,118 describe tobacco compositions which contain flavor release additives which, under cigarette smoking conditions, pyrolyze in a "retro-aldol" fragmentation reaction into products which enhance the flavor and aroma of the cigarette smoke.

SUMMARY OF THE INVENTION

The present invention provides compounds which upon thermolysis, hydrolysis or both, release an odorant molecule. They find utility, for example, in tobacco, tobacco paper, and as additives to food, beverages or gum.

These compounds are dicarboalkoxy dioxolane derivatives having the following formula:

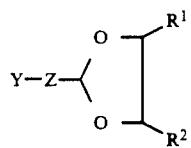

wherein $R^1$ and $R^2$ are, independently, $-CO_2R^3$ wherein $R^3$ is $-H_3$ or lower alkyl, provided that in at least one of $R^1$ and $R^2$, $R_4$ is lower alkyl; wherein Z is a direct bond, or $-CH=C(R^4)-$; where R is an alkyl group; and Y is, when Z is a direct bond,

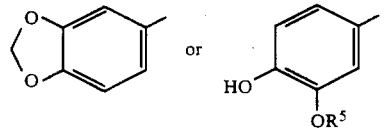

where $R^5$ is lower alkyl; and Y, when Z is $-CH=C(R^4)-$, is

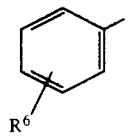

where $R^6$ is H, lower alkyl or $OR^7$, where $R^7$ is H or lower alkyl.

DEFINITIONS

As used throughout this specification, the term "organoleptic" refers to compounds of the invention which stimulate the sense of smell or taste, and are thus perceived as having a characteristic odor, flavor or both.

The terms "odor," "fragrance," and "smell" are used interchangeably whenever a compound is referred to as an organoleptic which is intended to stimulate the sense of smell. The terms "flavor," "flavoring," and "flavorant" are also used interchangeably whenever an organoleptic compound is referred to which is intended to stimulate the sense of taste.

An "organoleptically effective amount" is a level or amount of a compound or compounds of the invention present in a material at which the incorporated compound or compounds exhibit a sensory effect.

The terms "tobacco," and "tobacco substitutes" are used in the conventional sense and include smokable as well as non-smokable forms in which tobacco is regularly used, e.g., cigarettes, snuff, chewable compositions and the like.

Alkyl (including the alkyl portion of alkoxy and alkylthio)- a branched or unbranched saturated carbon chain containing 1 to 12 carbon atoms with lower alkyl representing a chain containing 1 to 6 carbon atoms.

DESCRIPTION OF THE INVENTION

The compounds of the invention can be readily prepared by methods known to those skilled in the art. The usual method involves condensation of an aldehyde with diethyl tartrate (or some other lower alkyl tartrate) in an inert solvent in the presence of an acid catalyst. During the condensation water is usually removed.

Either protic or Lewis acids may be used. Some acids which may be used are p-toluenesulfonic acid, sulfuric acid, phosphoric acid, hydrochloric acid, methanesulfonic acid, pyridinium p-toluenesulfonate, ferric chloride, acidic clay, acidic ion exchange resins, zinc chloride and titanium tetrachloride.

Preferred acids include p-toluenesulfonic acid, methanesulfonic acid and pyridinium p-toluenesulfonate. The most preferred acid is p-toluenesulfonic acid.

A variety of inert solvents may be used such as toluene, benzene, xylene, cyclohexane, hexane, dimethyl formamide, chlorobenzene and dichloroethane. The preferred solvents are toluene, xylene or dimethylformamide. The most preferred solvents are toluene and dimethylformamide.

The water formed in the reaction may be removed by azeotropic distillation or by interaction with a water scavenging agent such as a trialkyl orthoformate (alkyl is C1 to C5 and is usually the same as the lower alkyl in the tartrate), molecular sieves, sodium sulfate and the like.

In addition, the compounds of the invention may be prepared by first converting the aldehydes of the invention to the corresponding di-lower alkyl acetals (lower alkyl should be the same as the lower alkyl in the desired tartrate). Reaction of the acetals with a dialkyl tartrate under the conditions similar to that used when starting with an aldehyde will result in formation of the compounds of the invention.

The compounds of the invention may be used as flavorants in tobacco compositions, as sustained release odorants to mask or enhance the odors of burning tobacco products, in beverages, in microwaveable foods as flavor additives, and in the preparation of chewing gums.

The compounds of the invention are virtually odorless and tasteless under normal temperatures and atmospheric conditions, i.e., about 10–50 degrees Celcius and about 20 to 100% relative humidity, and exist as stable solids. However, when heated to higher temperatures, i.e., about 70 to about 300 degrees Celcius, in the presence of moisture or steam, they undergo a transformation in which the aldehyde is released. Illustrative examples of preferred species are shown below:

(4R,5R)-2-(3-Ethoxy-4-hydroxy-phenyl)-4,5-dicarboethoxy-1,3-dioxolane

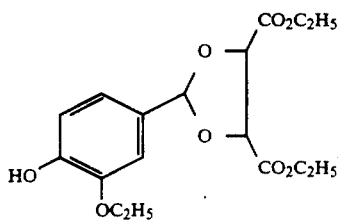

(4R,5R)-2-(3-Methoxy-4-hydroxy-phenyl)-4,5-dicarboethoxy-1,3-dioxolane

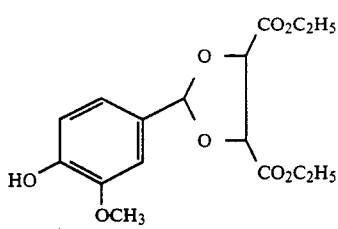

(4R,5R)-2-(3,4-Methylenedioxyphenyl)-4,5-dicarboethoxy-1,3-dioxolane

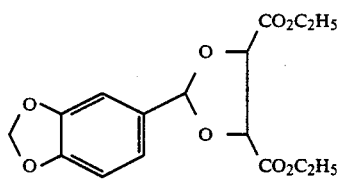

(4R,5R)-2-(3-Methoxy-4-hydroxy-phenyl)-4,5-dicarbomethoxy-1,3-dioxolane

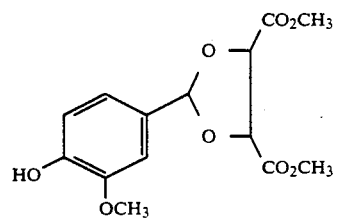

(E)-(4R,5R)-2-(1-Hexyl-2-phenyl-1-ethenyl)-4,5-dicarbomethoxy-1,3-dioxolane

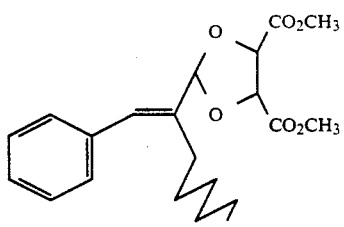

(E)-(4R,5R)-2-(1-Hexyl-2-phenyl-1-ethenyl)-4,5-dicarboethoxy-1,3-dioxolane

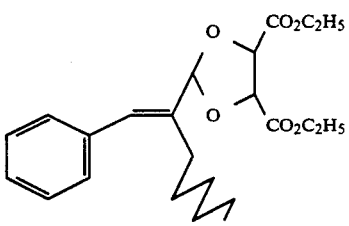

The compounds of the present invention are not limited to any particular stereoisomer and all possible stereoisomers are included within the scope of the invention.

Methods of preparation are described in the following publications:

P. Kocienski, et al., *Synthetic Comm.*, 1984, 14, pp. 1087–1092

L. A. Paquette et al., *J. Org. Chem.*, 1985, 50, pp. 5528–5533

M. Demuth et al., *J. Am. Chem. Soc.*, 1986, 108, pp. 4149–4154

Y. Maski et al., *Chem. Letters*, 1983, pp. 1835–1836

H. Yamamoto et al., *J. Am. Chem. Soc.*, 1985, 107, pp. 8254–8256

T. W. Green, "Protective Groups in Organic Synthesis," Chapter 4, John Wiley & Sons, New York, 1981

The compounds of the present invention possess organoleptic properties and therefore permit the development of methods useful in enhancing the flavor of foods. These compounds are also useful in enhancing the odor, masking any unpleasant odor or enhancing the flavor of tobacco products.

These compounds may be used individually in an amount effective to enhance a characteristic flavor or odor of a material. More commonly, however, the compounds are mixed with other flavor or fragrance components in an amount sufficient to provide the desired flavor or odor characteristic.

The amount required to produce the desired, overall effect varies depending upon the particular compound chosen, the product in which it will be used, and the particular effect desired.

For example, depending upon the selection and concentration of the compound chosen, when added either singly or as a mixture to cigarette tobacco at levels ranging from about 5 ppm to about 50,000 ppm it tends to enhance the smoking flavor, mask undesirable smoking odor or both. An important property of these compounds is that the flavorant or odorant is covalently bound as a non-volatile compound and it is only when the tobacco product is ignited and burns that the flavorant or odorant is released.

Addition of the compounds of the invention either separately or as a mixture at levels ranging from about 5 ppm to about 50,000 ppm by weight onto the media enclosing the tobacco serves to incorporate the odorant or flavorant in the side-stream smoke as the tobacco product burns. Air borne flavorants, odorants or both along with other combustion products are thus introduced. This newly formed odorant or flavorant serves to enhance or mask the smoking odors depending upon selection and use levels of the compounds.

The compounds of the present invention are particularly useful in the flavoring and aromatizing of certain cooked foods. For example, the compounds either singly or as a mixture added to cake batter impart an appropriate baking aroma to the cake as it is heated, as well as impart a flavor to the finished product. Typically, the compounds are employed at levels ranging from about 0.05 to about 5.00%.

The flavor of chewing gum may be enhanced by the addition of compounds of the present invention. A selected compound or mixture of compounds are kneaded into a gum base at levels ranging from about 0.1 to about 10.0% by weight. The appropriate flavors are released in the resulting gum upon mastication.

The compounds of the present invention may be incorporated in the foodstuff or tobacco product along with other ingredients. Such other ingredients include emulsifiers, carriers, binders, sweeteners, stabilizers, buffers and solvents.

The following examples serve to illustrate embodiments of the invention and the advance over the prior art. The examples are presented to illustrate and not to limit the scope of the invention.

All parts, proportions, percentages, and ratios used in the examples are by weight unless otherwise indicated.

EXAMPLES

Example 1

(4R,5R)-2-(3-Ethoxy-4-hydroxy-phenyl)-4,5-dicarboethoxy-1,3-dioxolane.

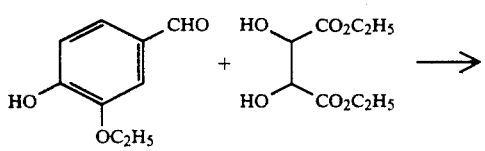

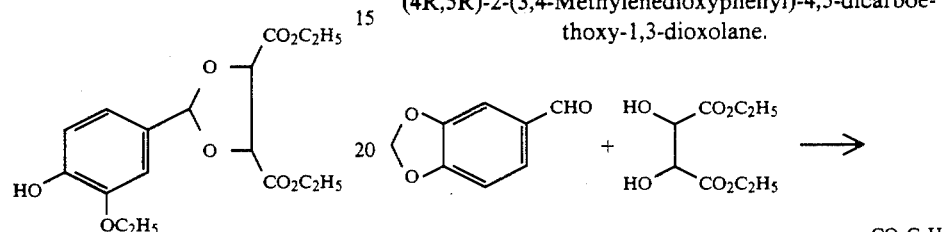

A mixture of diethyl L-tartrate (309 g, 1.5 mol), ethyl vanillin (166 g, 1 mol), toluene (2 L) and p-toluenesulfonic acid (5 g, 0.026 mol) was heated at 115°–116° C. for 24 hours under a nitrogen atmosphere. During the reaction, water was removed by azeotropic distillation via a Dean-Stark trap. The mixture was washed sequentially with saturated sodium bicarbonate solution (500 mL), brine (2×1 L) and dried over sodium sulfate. The solvent was evaporated under reduced pressure and the solid obtained was recrystallized from isopropanol to provide 120 g (34% yield) of (4R,5R)-2-(3-ethoxy-4-hydroxy-phenyl)-4,5-dicarboethoxy-1,3-dioxolane, mp 78°–80° C., $[\alpha]_D^{25} -38.0°$ (c,1.0; methanol). $^1$H-NMR (CDCl$_3$) δ7.17 (1H, d,J=1.8 Hz), 7.06 (1H,dd,J=1.8 Hz and 8.10 Hz), 6.91 (1H,d,J=8.2 Hz), 6.07 (1H,s), 5.83 (1H,s), 4.91, (1H,d,J=4.0 Hz), 4.80 (1H,d,J=4.0 Hz), 4.37–4.25 (4H, 2q, overlapping, J=7.2 Hz), 4.15 (2H,q,J=7.0 Hz), 1.45 (3H,t,J=7.0 Hz), 1.38–1.29 (6H,2t, overlapping J=7.2 Hz). IR (KBr) 3390, 2980, 2930, 1735, 1600 cm$^{-1}$. MS m/e (% abundance) 354 (55), 326 (3), 281 (40), 182 (85), 167 (85), 154 (100), 137 (70), 110 (30), 93 (10), 81 (10), 53 (5).

Example 2

(4R,5R)-2-(3-Methoxy-4-hydroxy-phenyl)-4,5-dicarboethoxy-1,3-dioxolane.

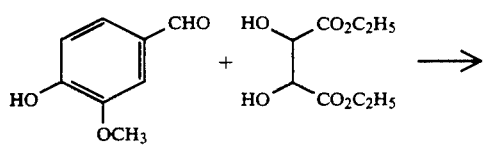

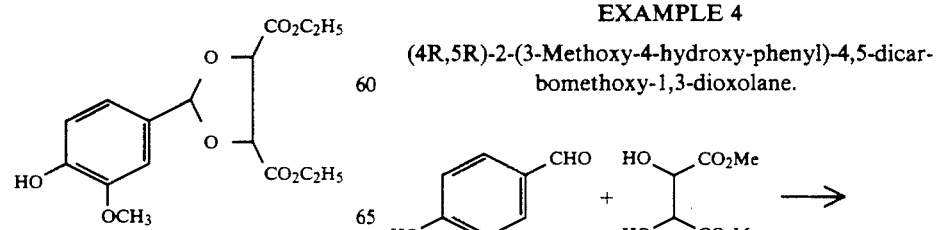

In a fashion similar to that described in Example 1, vanillin was condensed with diethyl L-tartrate to provide (4R,5R)-2-(3-methoxy-4-hydroxy-phenyl)-4,5-dicarboethoxy-1,2-dioxolane, mp 62°–64° C., $[\alpha]_D^{25} -41.7°$ (c, 1.5, methanol). $^1$H-NMR (CDCl$_3$) δ7.20 (1H,d,J=1.8 Hz), 7.03 (1H,dd,J=1.8 Hz and 8 Hz), 6.90 (1H,d,J=8 Hz), 6.09 (1H,s), 5.88 (1H,s), 4.92 (1H,d,J=3.8 Hz), 4.81 (1H,d,J=3.8 Hz), 4.36–4.24 (4H, 2q, overlapping, J=7.1 Hz), 3.90 (3H,s), 1.38–1.28 (6H, 2 t, overlapping, J=7.1 Hz). IR (KBr) 3500, 2970, 1740, 1605 cm$^{-1}$. MS m/e (% abundance) 340 (2), 267 (14), 168 (100), 151 (95), 137 (50), 109 (10), 65 (10), 43 (6).

Example 3

(4R,5R)-2-(3,4-Methylenedioxyphenyl)-4,5-dicarboethoxy-1,3-dioxolane.

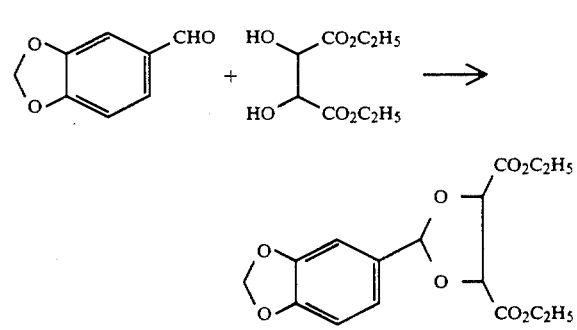

A mixture of piperonal (60 g, 0.4 mol), triethyl orthoformate (59.2 g, 0.4 mol), toluene (250 mL) and p-toluenesulfonic acid (2 g, 0.01 mol) was heated at 100°–110° C. for 0.5 h. Diethyl L-tartrate (103 g, 0.5 mol) was added to the hot solution over a 10 min. period. The mixture was then heated at reflux for 2 h. Subsequently over a 3 hour period, distillate (150 mL) was collected (pot temperature 84° C. to 110° C.). The mixture was cooled (25° C.) and washed with sodium bicarbonate solution (2×50 mL) and brine (1×50 mL). Evaporation of solvents under reduced pressure provided 130.7 g of crude product. Recrystallization from methanol provided 90 g (67% yield) of (4R,5R)-2-(3,4-methylenedioxyphenyl)-4,5-dicarboethoxy-1,3-dioxolane, mp 39°–40° C., $[\alpha]_D -34.8°$ (c, 1.0 methanol). $^1$H-NMR (CDCl$_3$) δ7.12 (1H, d, J=1.5 Hz), 7.03 (1H, dd, J=1.5 Hz and 7.9 Hz), 6.80 (1H, d, J=7.9 Hz), 6.06 (1H, s), 5.97 (2H, s), 4.91 (1H, d, J=4.0 Hz), 4.80 (1H, d, J=4.0 Hz), 4.36–4.26 (4H, 2 q, overlapping, J=7.0 Hz), 1.38–1.30 (6H, 2 t, overlapping, J=7.0 Hz). IR (KBr) 2980, 2900, 1735, 1490, 1445, 1415 cm$^{-1}$. MS m/e (% abundance) 338 (3), 265 (16), 166 (100), 149 (96), 135 (54), 121 (35), 93 (10), 65 (12), 43 (8).

EXAMPLE 4

(4R,5R)-2-(3-Methoxy-4-hydroxy-phenyl)-4,5-dicarbomethoxy-1,3-dioxolane.

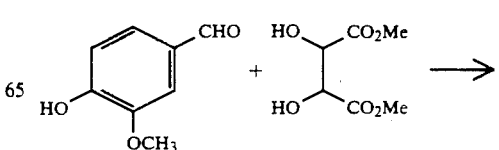

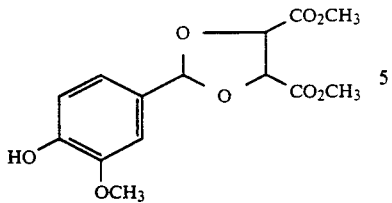

In a fashion similar to that described for Example 3, vanillin and dimethyl L-tartrate were condensed to provide (4R,5R)-2-(3-methoxy-4-hydroxy-phenyl)-4,5-dicarbomethoxy-1,3-dioxolane, mp 88°–90° C., $[\alpha]_D^{25} -35.1°$ (c, 0.1, methanol). $^1$H-NMR (CDCl$_3$) δ7.20 (1H, d, J=1.8 Hz), 7.06 (1H, dd, J=1.8 Hz and 8.2 Hz), 6.19 (1H, d, J=8.2 Hz), 6.08 (1H,s), 5.82 (1H, s), 4.96 (1H, d, J=3.8 Hz), 4.85 (1H, d, J=3.8 Hz), 3.91 (3H,s), 3.87 (3H,s), 3.84 (3H,s). IR (film) 3450, 1750, 1600, 1510, 1460, 1430 cm$^{-1}$. Ms m/e (% abundance) 313(2), 312(12), 253(40), 168(84), 151(100), 124(22), 109(14), 59(18).

EXAMPLE 5

(E)-(4R,5R)-2-(1-Hexyl-2-phenyl-1-ethenyl)-4,5-dicarbomethoxy-1,3-dioxolane.

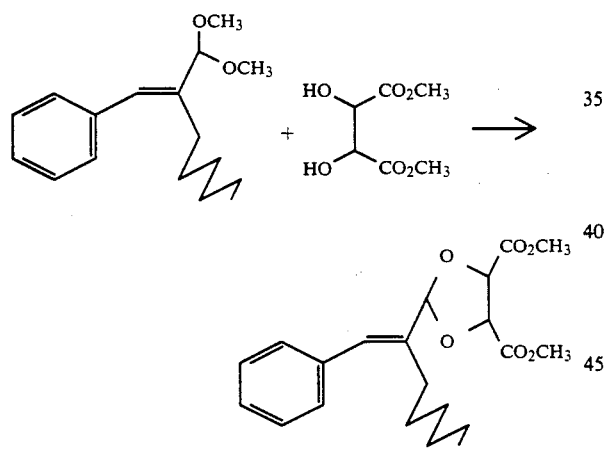

In a fashion similar to that described in Example 4, α-hexylcinnamaldehyde dimethyl acetal and dimethyl L-tartrate were condensed to provide a mixture of (E)- and (Z)-(4R,5R)-2-(1-hexyl-2-phenyl-1-ethenyl)-4,5-dicarbomethoxy-1,3-dioxolane in an approximate ratio of 90:10 Crystallization provided the pure E-isomer, mp 49°–50° C., $[\alpha]_D^{25} -2.2$ (c, 0.2, methanol). $^1$H-NMR (CDCl$_3$) δ7.35–7.26 (5H,m), 6.74 (1H,s), 5.84 (1H,s) 4.86 (1H, d, J=4.4 Hz), 4.70 (1H, d, J=4.4 Hz), 3.85 (3H,s), 3.80 (3H,s), 2.34–2.27 (2H,m), 1.58–1.55 (2H,m), 1.37–1.26 (6H,m), 0.93–0.87 (3H,m), IR (KBr) 2900, 2840, 1730, 1430, 1340, 1200, 1100, 1060, 1030, 980, 950, 915, 870, 790, 750, 730, 690 cm$^{-1}$. MS m/e (% abundance) 305 (4), 292 (17), 291 (100), 145 (18), 142 (25), 131 (73), 129 (76), 128 (26), 117 (74), 116 (17), 115 (51), 104 (29), 91 (57), 59 (31), 41 (25).

EXAMPLE 6

(E)-(4R,5R)-2-(1-Hexyl-2-phenyl-1-ethenyl)-4,5-dicarboethoxy-1,3-dioxolane

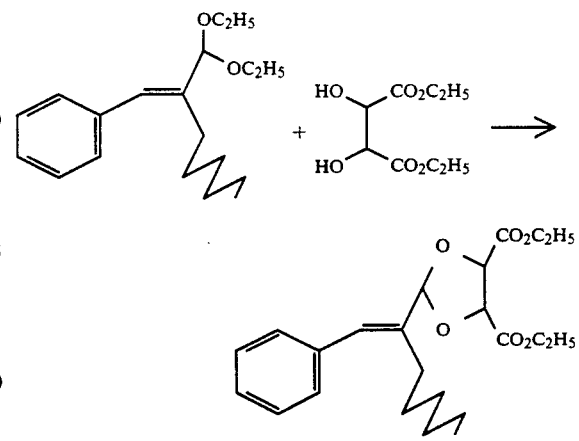

In a fashion similar to that described in Example 4,α-hexylcinnamaldehyde diethyl acetal and diethyl L-tartrate were condensed to provide a mixture of (E)- and (Z)-(4R,5R)-2-(1-hexyl-2-phenyl-1-ethenyl)-4,5-dicarboethoxy-1,3-dioxolane. Low temperature crystallization provided the pure E-isomer, $[\alpha]_D^{25} -5.9$ (c, 0.1, methanol). $^1$-H-NMR (CDCl$_3$) δ7.35–7.26 (5H,m), 6.75 (1H,s), 5.65 (1H,s), 4.87 (1H, d, J=4.5 Hz), 4.74 (1H, d, J=4.5 Hz), 4.36–4.25 (4H, 2 q, overlapping, J=7.1 Hz), 2.38–2.32 (2H,m), 1.58–1.57 (2H,m), 1.38–1.25 (6H, 2 t, overlapping, J=7.1 Hz), 1.38–1.22 (6H,m) 0.88–0.83 (3H, m). IR (film) 2900, 2840, 1750, 1450, 1360, 1260, 1200, 1100, 1010, 940, 900, 840, 730, 680 cm$^{-1}$. MS m/e (% abundance) 404 (0.6), 333 (4), 320 (18), 319 (100), 143 (21), 142 (38), 131 (80), 129 (88), 128 (28), 117 (78), 115 (52), 104 (31), 91 (56), 43 (27).

EXAMPLE 7

Preparation of a Vanillin Cigarette

A 1% ethanolic solution of the compound from Example 1 was applied to cigarette papers at the rate of 100 ppm. (Application rates from 5 to 50,000 ppm may be useful). The paper was incorporated into cigarettes. Prior to smoking, no odor of vanillin was observed. Upon smoking a strong, distinctly vanillin odor was observed in the room air.

EXAMPLE 8

Preparation of a Cigarette Containing Vanillin Flavored Tobacco

A 1% ethanolic solution of the product of Example 1 was injected into the tobacco of a typical American Blend cigarette at a level of 100 ppm. Prior to smoking, no odor or vanillin was observed. Upon smoking, the mainstream and sidestream smoke displayed a strong vanillin odor.

EXAMPLE 9

Preparation of an α-Hexyl Cinnamic Aldehyde Cigarette

A 1% ethanolic solution of the compound from Example 8 was applied to cigarette papers at the rate of 100 ppm. The paper was incorporated into cigarettes. Prior to smoking, no odor of α-hexyl cinnamic aldehyde was observed. Upon smoking a slight (but distinct), pleasant jasmine-like floral odor was observed in the room air.

We claim:

1. Dicarboalkoxy dioxolane derivatives, comprising compounds represented by the formula:

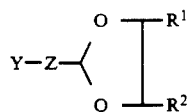

wherein $R^1$ and $R^2$ may be the same or different and are represented by the formula $-CO_2R^3$, wherein $R^3$ is selected from the group consisting of hydrogen and lower alkyl, provided that in at least one of $R^1$ and $R^2$, $R^3$ is lower alkyl; Z is a direct bond or $-CH=C(R^4)-$, wherein $R^4$ is n-hexyl; and Y is represented by the formula, when Z is a direct bond,

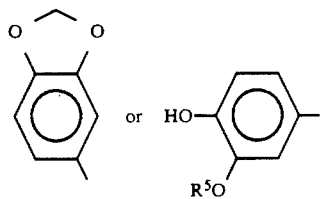

wherein $R^5$ is lower alkyl; and Y is represented by the formula, when Z is $-CH=C(R^4)-$,

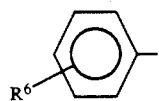

wherein $R^6$ may be the same or different and is selected from the group consisting of hydrogen, lower alkyl, and $OR^7$, wherein $R^7$ is selected from the group consisting of hydrogen and lower alkyl.

2. The dicarboalkoxy dioxolane derivative according to claim 1, wherein Z is a direct bond.

3. The dicarboalkoxy dioxolane derivative according to claim 2, wherein $R^5$ is selected from the group consisting of methyl and ethyl.

4. The dicarboalkoxy dioxolane derivative according to claim 1, wherein Z is $-CH=C(R^4)-$.

5. The dicarboalkoxy dioxolane derivative according to claim 1, wherein the derivative has the name:
2-(3-Ethoxy-4-hydroxy-phenyl)-4,5-dicarboethoxy-1,3-dioxolane
2-(3-Methoxy-4-hydroxy-phenyl)-4,5-dicarboethoxy-1,3-dioxolane
2-(3,4-Methylenedioxyphenyl)-4,5-dicarboethoxy-1,3-dioxolane
2-(3-Methoxy-4-hydroxy-phenyl)-4,5-dicarbomethoxy-1,3-dioxolane
2-(1-Hexyl-2-phenyl-1-ethenyl)-4,5-dicarbomethoxy-1,3-dioxolane, or
2-(1-Hexyl-2-phenyl-1-ethenyl)-4,5-dicarboethoxy-1,3-dioxolane.

6. The dicarboalkoxy dioxolane derivative according to claim 5, wherein the derivative has the name:
2-(3-Ethoxy-4-hydroxy-phenyl)-4,5-dicarboethoxy-1,3-dioxolane
2-(3-Methoxy-4-hydroxy-phenyl)-4,5-dicarboethoxy-1,3-dioxolane
2-(3,4-Methylenedioxyphenyl)-4,5-dicarboethoxy-1,3-dioxolane, or
2-(3-Methoxy-4-hydroxy-phenyl)-4,5-dicarbomethoxy-1,3-dioxolane.

7. The dicarboalkoxy dioxolane derivative according to claim 5, wherein the derivative has the name:
2-(1-Hexyl-2-phenyl-1-ethenyl)-4,5-dicarbomethoxy-1,3-dioxolane, or
2-(1-Hexyl-2-phenyl-1-ethenyl)-4,5-dicarboethoxy-1,3-dioxolane.

8. The dicarboalkoxy dioxolane derivative according to claim 5, wherein the derivative has the name:
(4R,5R)-2-(3-Ethoxy-4-hydroxy-phenyl)-4,5-dicarboethoxy-1,3-dioxolane
(4R,5R)-2-(3-Methoxy-4-hydroxy-phenyl)-4,5-dicarboethoxy-1,3-dioxolane
(4R,5R)-2-(3,4-Methylenedioxyphenyl)-4,5-dicarboethoxy-1,3-dioxolane
(4R,5R)-2-(3-Methoxy-4-hydroxy-phenyl)-4,5-dicarbomethoxy-1,3-dioxolane
(E)-(4R,5R)-2-(1-Hexyl-2-phenyl-1-ethenyl)-4,5-dicarbomethoxy-1,3-dioxolane, or
(E)-(4R,5R)-2-(1-Hexyl-2-phenyl-1-ethenyl)-4,5-dicarboethoxy-1,3-dioxolane.

9. The dicarboalkoxy dioxolane derivative according to claim 8, wherein the derivative has the name:
(4R,5R)-2-(3-Ethoxy-4-hydroxy-phenyl)-4,5-dicarboethoxy-1,3-dioxolane
(4R,5R)-2-(3-Methoxy-4-hydroxy-phenyl)-4,5-dicarboethoxy-1,3-dioxolane
(4R,5R)-2-(3,4-Methylenedioxyphenyl)-4,5-dicarboethoxy-1,3-dioxolane, or
(4R,5R)-2-(3-Methoxy-4-hydroxy-phenyl)-4,5-dicarbomethoxy-1,3-dioxolane.

10. The dicarboalkoxy dioxolane derivative according to claim 8, wherein the derivative has the name:
(E)-(4R,5R)-2-(1-Hexyl-2-phenyl-1-ethenyl)-4,5-dicarbomethoxy-1,3-dioxolane, or
(E)-(4R,5R)-2-(1-Hexyl-2-phenyl-1-ethenyl)-4,5-dicarboethoxy-1,3-dioxolane.

* * * * *